US00PP10026P

United States Patent [19]

Vlielander

[11] Patent Number: Plant 10,026

[45] Date of Patent: Sep. 9, 1997

[54] KALANCHOE PLANT NAMED 'MOUNT LOA'

[75] Inventor: Ike Vlielander, De Lier, Netherlands

[73] Assignee: Fides Beheer B.V., De Lier, Netherlands

[21] Appl. No.: 618,258

[22] Filed: Mar. 18, 1996

[51] Int. Cl.[6] ..... A01H 5/00

[52] U.S. Cl. ..... Plt./87.15

[58] Field of Search ..... Plt./87.15

[56] References Cited

U.S. PATENT DOCUMENTS

P.P. 5,961 4/1987 Mikkelsen ..... Plt./87.15

P.P. 8,997 11/1994 Hope ..... Plt./87.15

*Primary Examiner*—Howard J. Locker

*Attorney, Agent, or Firm*—C. A. Whealy

[57] ABSTRACT

A distinct cultivar of Kalanchoe plant named Mount Loa, characterized by its bright orange flower color; moderately vigorous plant growth habit; freely branching habit; proportional leaf size to plant size; uniform plant habit and inflorescence display; early flowering; floriferousness; and excellent postproduction longevity.

1 Drawing Sheet

The present invention relates to a new and distinct cultivar of Kalanchoe plant, botanically known as *Kalanchoe blossfeldiana*, and hereinafer referred to by the cultivar name Mount Loa.

The new cultivar is a product of a planned breeding program conducted by the inventor in De Lier, The Netherlands. The objective of the breeding program was to create new Kalanchoe cultivars having a uniform plant habit, good flower and foliage colors, and flowers and foliage with good substance.

The new cultivar originated from a cross made by the inventor of the Kalanchoe cultivar Nevada (not patented) as the male or pollen parent with the Kalanchoe cultivar Viti (not patented) as the female or seed parent.

The cultivar Mount Loa was discovered and selected by the inventor as a flowering plant within the progeny of the stated cross in a controlled environment in De Lier, The Netherlands. Asexual reproduction of the new cultivar by terminal cuttings taken at De Lier, The Netherlands, has shown that the unique features of this new Kalanchoe are stabilized and reproduced true to type in successive generations.

The cultivar Mount Loa has not been observed under all possible environmental conditions. The phenotype may vary somewhat with variations in environment such as temperature, daylength and light intensity, without, however, any variance in genotype. The following observations, measurements and comparisons describe plants grown in De Lier, The Netherlands, under commercial practice in a glass-covered greenhouse with day temperatures ranging from 19 to 21C and night temperatures of 18 to 19C.

The following traits have been repeatedly observed and are determined to be in the unique characteristics of Mount Loa. These characteristics in combintion distinguish Mount Loa as a new and distinct cultivar:

1. Bright orange flower color.
2. Moderately vigorous plant growth habit.
3. Freely branching habit with shoots forming at every node. Plants do not require pinching.
4. Proportional leaf size to plant size.
5. Suitable for various container sizes from 9 to 11 cm.
6. Uniform plant habit and inflorescence display.
7. Early flowering.
8. Floriferous with numerous flowers per plant.

9. Excellent postproduction longevity. Petal color does not fade significantly as flowers age.

Plants of the cultivar Mount Loa are most similar in petal color to the male parent, the cultivar Nevada. The new Kalanchoe differs from the parent cultivar Nevada in the following characeristics:

1. Plants of the cultivar Mount Loa are more uniform in plant habit and inflorescence display than plants of the cultivar Nevada.
2. Plants of the cultivar Mount Loa have shorter lateral branches and internodes than plants of the cultivar Nevada.
3. Plants of the cultivar Mount Loa have larger leaves than plants of the cultivar Nevada.
4. Plants of the cultivar Mount Loa flower several days earlier than plants of the cultivar Nevada.
5. Petal color of plants of the cultivar Mount Loa is slightly darker than the petal color of plants of the cultivar Nevada.
6. Flowers of plants of the cultivar Mount Loa last longer than flowers of plants of the cultivar Nevada.

A detailed comparison of the cultivars Mount Loa and Nevada appears in Chart A at the end of the specification.

The cultivar Mount Loa differs from the female parent, the cultivar Viti, in the following characteristics:

1. Plants of the cultivar Mount Loa are more uniform in plant habit and inflorescence display than plants of the cultivar Viti.
2. Plants of the cultivar Mount Loa are larger than plants of the cultivar Viti.
3. Plants of the cultivar Mount Loa have more flowers than plants of the cultivar Viti.
4. The petal color of plants of the cultivar Mount Loa is bright orange whereas the petal color of plants of the cultivar Viti is dark pink.

The accompanying colored photograph illustrates the overall appearance of the new cultivar, showing the colors as true as it is reasonably possible to obtain in colored reproductions of this type. The photograph comprises a top perspective view of a typical potted plant on Mount Loa taken under natural light conditions at approximately noon in De Lier, The Netherlands.

In the following description, color references are made to The Royal Horticultural Society Colour Chart except where general terms of ordinary dictionary significance are used.

Measurements and numerical values represent averages for twelve typical plants in 10.5-cm containers and treated with daminozide growth retardant at a rate of 4 grams per liter.

Botanical classification: *Kalanchoe blossfeldiana* cultivar Mount Loa.

Parentage:

*Male or pollen parent.*—*Kalanchoe blossfeldiana* cultivar Nevada (not patented).

*Female or seed parent.*—*Kalanchoe blossfeldiana* cultivar Viti (not patented).

Propagation:

*Type cutting.*—Terminal cuttings.

*Time to initiate roots.*—12 days at 21C soil temperature.

*Rooting habit.*—Numerous, fine, fibrous, and well-branched.

Plant description:

*Form.*—Upright and uniform. Plant shape is an inverted triangle with a rounded apex. Actual plant shape will depend on whether or not plants are pinched (vegetative terminals removed).

*Branching habit.*—Freely branching, generally shoots formed at every node. Typically 5 to 6 lateral branches will develop with 8 to 13 leaves each.

*Plant height at flowering.*—From soil level to top of plant, 19 cm, appropriate for 9 to 11-cm containers.

*Vigor.*—Moderately vigorous and moderate growth rate.

*Crop time.*—Three to four weeks of long day/short night conditions followed by 7.5 to 11 weeks of short day/long night conditions are required to produce flowering plants. Depending on temperature and light levels, a total of 10.5 to 15 weeks is required.

*Foliage description.*—Leaves simple, opposite, generally symmetrical. Size: Length: 11.5 cm. Width: 9 cm. Shape: Elliptic. Apex: Acute to obtuse. Base: Acute. Margin: Crenate. Texture: Leathery, glabrous, coriaceous and succulent. Petiole length: 1.4 cm. Color: Young foliage upper side: 147A. Young foliage under side: 147B. Mature foliage upper side: 147A. Mature foliage under side: 147B. Petiole: 147A. Stem color: 147A. Venation upper side: 147A/147B. Venation underside: 147B.

Flower description:

*Flower type and habit.*—Single flowers arranged in panicles, compound dichasial cymes on strong peduncles. Freely flowering and very floriferous with new buds continuing to develop. Uniform inflorescence display.

*Natural flowering season.*—Autumn/winter in Northern Hemisphere. Flower initiation and development can be induced under short day/long night conditions. Opening of new buds will continue for at least seven weeks. Individual flowers last about 23 days after opening. Flowers persistent.

*Inflorescences borne.*—Above foliage, arising from leaf axils. Inflorescence of each shoot is formed by dichotomous branching.

*Time to flower.*—Under warm growing temperatures, 25C, plants of the cultivar Mount Loa will start flowering after 7.5 weeks of exposure to controlled photoperiods (short day/long night conditions). Under cooler growing temperatures, 20C, plants of the cultivar Mount Loa will flower after 11 weeks of exposure to controlled photoperiods. First flower open is the terminal flower at the main axis and is followed by the opening of the terminal flowers of the side branches of the inflorescence.

*Flower diameter.*—1.5 cm.

*Flower depth (height).*—1.5 cm.

*Quantity.*—At least 150 flowers per plant.

*Flower buds.*—Size: Length: 8 mm. Width: 3.5 mm. Shape: Oblong becoming tubular/ovoid with development. Rate of opening: Relatively rapid. Color: Initially 138C becoming 33D just before opening.

*Petals.*—Quantity: 4 fused at base to form bell-shaped corolla. Size: Length: 7 mm. Width: 4.5 mm. Shape: Ovate. Apex: Acute. Margin: Entire. Texture: Glabrous, smooth and satiny. Aspect: Flat to somewhat upright. Color: When opening: 34A. Mature, upper side: 33A. Mature, under side: 29D/33D. Fading to: 40C. After senescence: 40C/40D.

*Sepals.*—Quantity: 4. Shape: Oblong, pointed. Apex: Acute. Margin: Entire. Texture: Glabrous. Aspect: Upright, rigid. Color: Upper side: 138D, glossy. Under side: 138D, glossy.

*Calyx.*—Size: 10.5 mm. Shape: Funnel. Texture: Glabrous. Color: 29D/138D.

*Peduncle.*—Aspect: Strong, erect, rigid, and upright. Length: 3 to 5 mm. Texture: Glabrous. Color: 138B.

*Reproductive organs.*—Stamens: Stamen number: 8. Anther size: 0.3 mm. Anther shape: Flat, elliptic. Anther color: Approximately 150D. Pollen color: Approximately 12A. Pistils: Pistil number: 4. Stigma shape: Flat. Stigma appearance: Crystalline. Stigma color: 8D. Style length: 1.1 cm. Style color: 138D. Ovary number: 4-celled. Ovary color: Green.

Disease resistance: No known Kalanchoe diseases observed to date.

Seed production: Seed production has not been observed.

CHART A

| CHARACTERISTIC | MOUNT LOA | NEVADA |
|---|---|---|
| PLANT HEIGHT | 19 cm | 20 cm |
| GROWTH RATE | Moderate | Moderate |
| CROP TIME | 10.5 to 15 weeks | 11 to 17 weeks |
| TIME TO FLOWER | 7.5 to 11 weeks | 8 to 12 weeks |
| NUMBER OF LATERAL BRANCHES | 5 to 6 | 4 to 5 |
| LATERAL BRANCH LENGTH | 16 cm | 18 cm |
| QUANTITY OF LEAVES PER LATERAL BRANCH | 8 to 13 | 7 to 13 |
| LEAF LENGTH | 11.5 cm | 10.5 cm |
| LEAF WIDTH | 9 cm | 7.5 cm |
| FLOWER DIAMETER | 1.5 cm | 1.5 cm |
| FLOWER LONGEVITY | 23 days | 19 days |
| PETAL COLOR WHEN OPENING | 34A | 33A |
| MATURE PETAL COLOR, UPPER SIDE | 33A | 32A |
| MATURE PETAL COLOR, UNDER SIDE | 29D/33D | 29D/33D |
| PETAL COLOR, FADING TO | 40C | 40C |

It is claimed:

1. A new and distinct cultivar of Kalanchoe plant named Mount Loa, as illustrated and described.

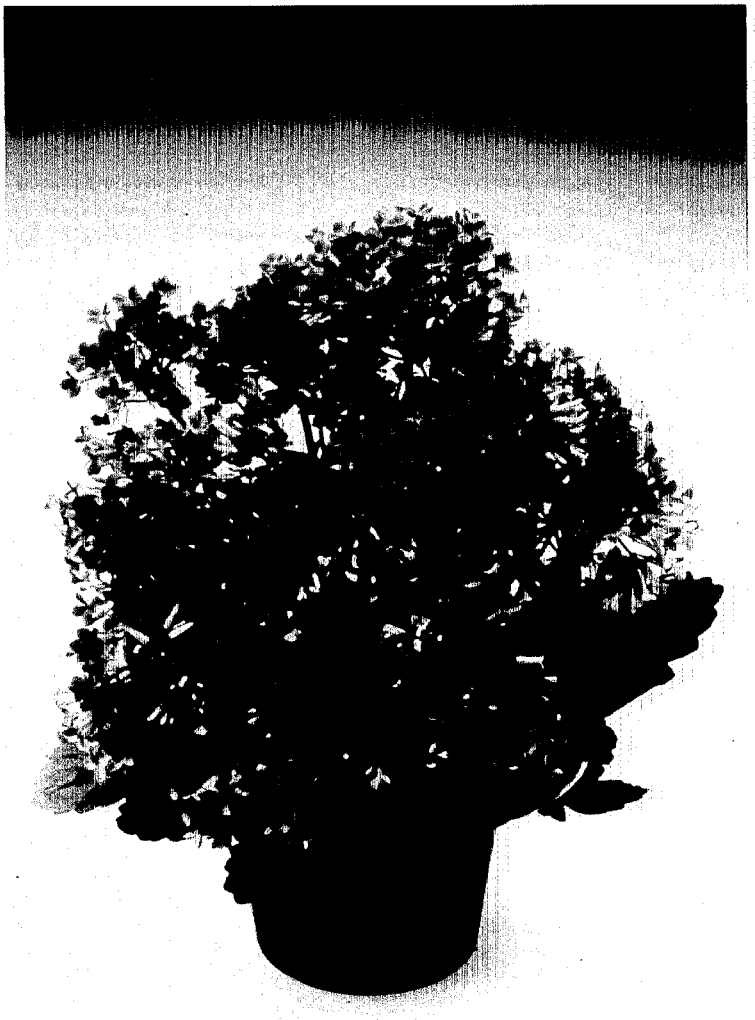

* * * * *